US010980430B2

(12) United States Patent
Przybyszewski et al.

(10) Patent No.: US 10,980,430 B2
(45) Date of Patent: Apr. 20, 2021

(54) CUFF-LESS MULTI-SENSOR SYSTEM FOR STATISTICAL INFERENCE OF BLOOD PRESSURE WITH PROGRESSIVE LEARNING/TUNING

(71) Applicant: HEALTHY.IO LTD., Tel Aviv-Jaffa (IL)

(72) Inventors: Piotr Przybyszewski, San Jose, CA (US); Eunseog Youn, San Jose, CA (US); Walter De Brouwer, Los Altos, CA (US); Brian G. La Plume, Santa Clara, CA (US); Babak Aghazadeh, Fremont, CA (US); Maxim Akhterov, Palo Alto, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 974 days.

(21) Appl. No.: 15/456,465

(22) Filed: Mar. 10, 2017

(65) Prior Publication Data

US 2017/0258340 A1    Sep. 14, 2017

Related U.S. Application Data

(60) Provisional application No. 62/306,626, filed on Mar. 10, 2016.

(51) Int. Cl.
*A61B 5/021* (2006.01)
*A61B 5/00* (2006.01)

(52) U.S. Cl.
CPC ........ *A61B 5/02141* (2013.01); *A61B 5/0022* (2013.01); *A61B 5/02125* (2013.01); *A61B 5/725* (2013.01); *A61B 5/7257* (2013.01); *A61B 5/7267* (2013.01); *A61B 5/7282* (2013.01); *A61B 5/0024* (2013.01); *A61B 2562/04* (2013.01)

(58) Field of Classification Search
CPC . A61B 5/021; A61B 5/02141; A61B 5/02108; A61B 5/02116; A61B 5/02125; A61B 5/02133; A61B 5/0022; A61B 5/0024
See application file for complete search history.

(56) References Cited

U.S. PATENT DOCUMENTS

2007/0265533 A1* 11/2007 Tran .................. A61B 5/021
600/481
2010/0217099 A1* 8/2010 LeBoeuf ............. A61B 5/0024
600/301

* cited by examiner

*Primary Examiner* — Carrie R Dorna
(74) *Attorney, Agent, or Firm* — Finnegan, Henderson, Farabow, Garrett & Dunner, LLP

(57) ABSTRACT

In one embodiment of the invention, a cuff-less blood pressure measuring system is disclosed including cuff-less blood pressure scanner with a vital signs signal processor having an adaptive blood pressure model. A machine learning process is further disclosed to tune the adaptive blood pressure model of the cuff-less blood pressure measuring system to the user.

20 Claims, 12 Drawing Sheets

CUFF-LESS MULTI-SENSOR SYSTEM FOR STATISTICAL INFERENCE OF BLOOD PRESSURE WITH PROGRESSIVE LEARNING/TUNING

CROSS-REFERENCE TO RELATED APPLICATIONS

This United States (U.S.) non-provisional patent application claims the benefit of U.S. Provisional Patent Application No. 62/306,626 filed on Mar. 10, 2016 by inventors Piotr Przybyszewski et al., titled CUFF-LESS MULTI-SENSOR SYSTEM FOR STATISTICAL INFERENCE OF BLOOD PRESSURE WITH PROGRESSIVE LEARNING/TUNING, incorporated herein by reference for all intents and purposes.

This United States (U.S.) patent application is related to U.S. patent application Ser. No. 14/641,303 filed on Mar. 6, 2015 by inventors Max Little, et al., entitled METHODS AND APPARATUS FOR SELF-CALIBRATING NON-INVASIVE CUFFLESS BLOOD PRESSURE MEASUREMENTS, incorporated herein by reference for all intents and purposes. This United States (U.S.) patent application is also related to U.S. patent application Ser. No. 14/704,961 filed on May 5, 2015 by inventors Bernard Burg, et al., entitled PORTABLE DEVICE WITH MULTIPLE INTEGRATED SENSORS FOR VITAL SIGNS SCANNING, incorporated herein by reference for all intents and purposes. This United States (U.S.) patent application is also related to U.S. patent application Ser. No. 14/292,820 filed on May 30, 2014 by inventors Wenyi Zhao, et al., entitled METHODS OF DATA ACQUISITION QUALITY AND DATA FUSION FOR PERSONAL PORTABLE WIRELESS VITAL SIGNS SCANNER, incorporated herein by reference for all intents and purposes.

FIELD

The embodiments of the invention relate generally to blood pressure (BP) measurement systems.

BACKGROUND

Blood pressure (systemic arterial blood pressure) is the pressure that circulating blood exerts against the walls of the blood vessels in the course of circulation, and is a good indication of the capacity of the blood vessels and of cardiac function in a body. Blood pressure may be measured in different ways and traditionally has units of millimeters of mercury (mmHg). Because arterial blood pressure varies as a waveform, referred to as an arterial pressure wave, measurements of interest are systolic blood pressure (SDP) (its peak) and diastole blood pressure (DBP) (its lowest point). Systolic blood pressure (SDP) is the maximum arterial pressure during contraction of heart as it beats and pushes blood out. Diastolic blood pressure (DI3P) refers to the lowest blood pressure within the arterial blood stream due to expansion of heart when pulling blood into the heart and it is not beating.

Blood pressure may be measured in various ways that may be characterized as invasive and non-invasive. One non-invasive technique of measuring blood pressure uses a sphygmomanometer, an inflatable cuff to collapse and then release the artery under the cuff in a controlled manner, and a pressure measurement device (e.g., manometer) to measure the pressure. The sphygmomanometer is sometimes referred to as a blood pressure cuff. A sphygmomanometer can provide fairly accurate readings of blood pressure. However, the use of a sphygmomanometer is rather intrusive and not very user friendly so it may not be used that often by a user to capture his/her blood pressure. It is desirable to provide an accurate cuff-less based system and method for determining blood pressure.

BRIEF DESCRIPTIONS OF THE DRAWINGS

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

It is desirable to provide an accurate cuff-less based system and method for determining blood pressure. Cuff-less methods for determining blood pressure often rely on a pulse-wave-transit-time model (or on its related quantities, such as pulse-arrival-time, pulse-velocity, etc.). Such methods typically involve measurement of ECG and PPG or multiple PPG signals from different sites of the body. By calculating the time it takes for a blood pressure pulse to travel between two points separated by a known distance within the cardio-vascular system, one can determine the average stiffness of vessels. This, in turn, can be used to estimate the systolic and diastolic blood pressures. However, these methods may require periodic calibration, because conversion coefficients often change over time and cannot be treated as a constant over long time periods. During calibrations of the conversion coefficients, recording of ECG and PPG or of multiple PPG signals is usually paired with a cuff-based measurement of blood pressure. Accordingly, there may be a number of disadvantages such as limited accuracy, requirement for relatively frequent re-calibrations, non-improvement of accuracy over time, and/or an inability to cover diverse range of physiological states. It is desirable to provide a cuff-less measurement system for the inference of blood pressure with periodic tuning, which overcomes one or more of these limitations.

Cuff-Less Blood Pressure Measurement System

Figure 1:
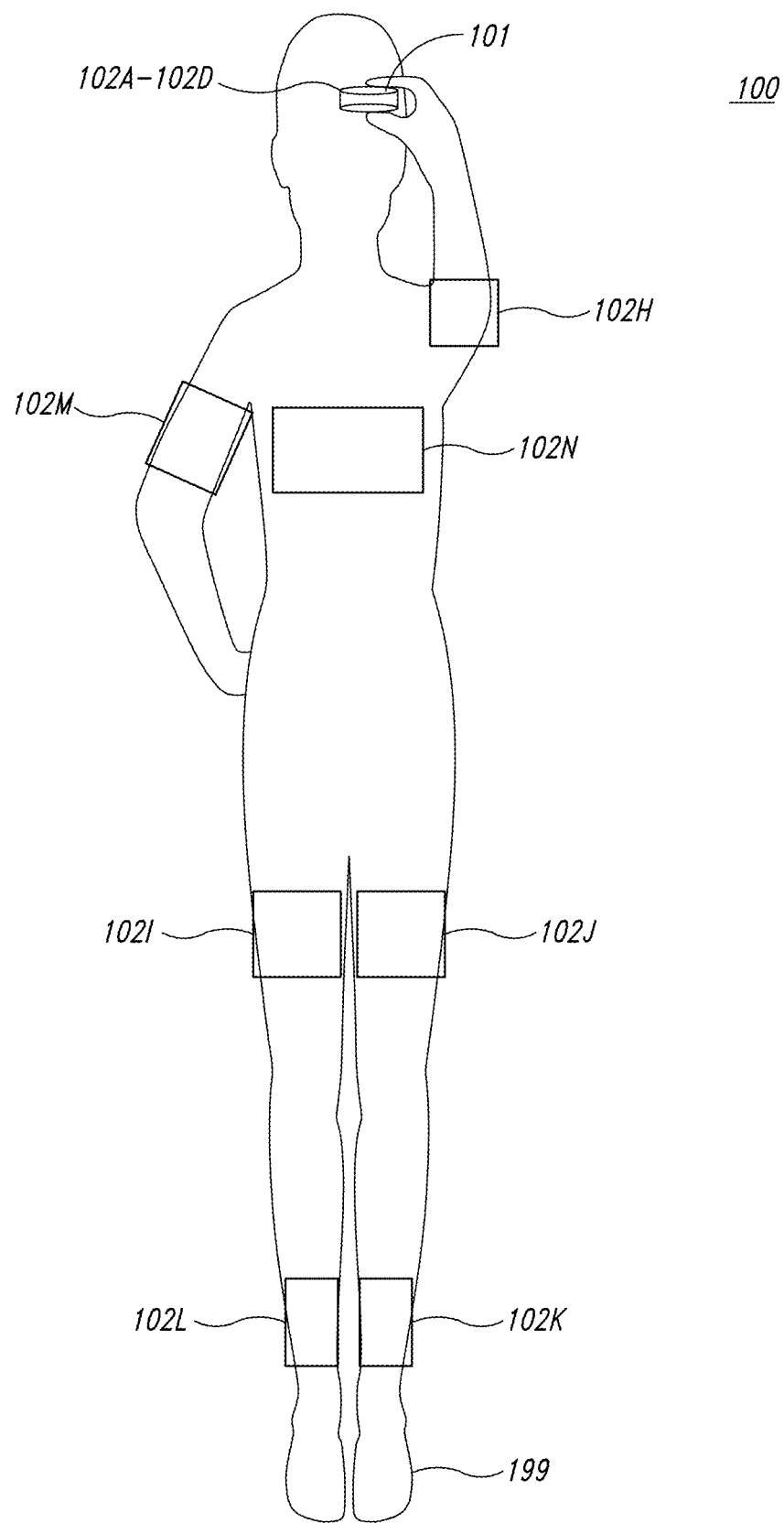
FIG. 1 is diagram of a cuff-less blood pressure measurement system coupled to a user body to non-invasively calculate blood pressure.

Referring now to FIG. 1, a cuff-less blood pressure measurement system 100 is shown including a centralized portable BP scanner 101 and a plurality of bio-sensors 102A-102N. The plurality of bio-sensors 102A-102N are in communication with a signal processor (e.g., signal processor 201 of FIG. 2) of the centralized portable BP scanner 101. A plurality of bio-sensors 102A-102D are local to the signal processor within a housing of the centralized portable BP scanner 101. A plurality of bio-sensors 102H-102N can be positioned at different points or sites on the user body 199, remote from the signal processor of the centralized portable BP scanner 101. For example, the remote bio-sensors 102H,102M may be located on the left and right arms respectively. The remote bio-sensors 102J,102I may be located on the left and right thighs respectively. The remote bio-sensors 102K,102L may be located on the left and right thighs respectively. One or more remote bio-sensors 102N may be located over or around the chest and/or back.

One or more of the plurality of remote bio-sensors 102H-102N may be in wireless communication with the signal processor of the centralized portable BP scanner 101 by radio receiver/transmitters. Alternatively, one or more of the plurality of remote bio-sensors 102L-102N may be in wired communication with the signal processor of the centralized portable BP scanner 101 by wire cables.

The plurality of bio-sensors 102A-102N may be optical sensors, electrical sensors (or their electrodes), motion sensors, acceleration sensors, piezo-electric sensors, acoustic sensors, and/or combinations thereof. Some may include a stimulator induced upon the body of the user such as wavelengths of light or photons for example, from one or more LEDs or semiconductor lasers. The plurality of bio-sensors 102A-102N include an electrical electro-cardiogram (ECG) sensor, multiple optical photo-plethysmograph (PPG) sensors located at different positions upon the users body (multi-site), an electrical impedance plethysmograph (IPG) sensor, a piezo-electric BCG sensor, an accelerometer sensor, a pressure sensor, ultrasound imaging sensor, ultrasound Doppler sensor, laser Doppler sensor, far infra-red (IR) imaging sensor, specular imaging sensor, etc.

Figure 2:
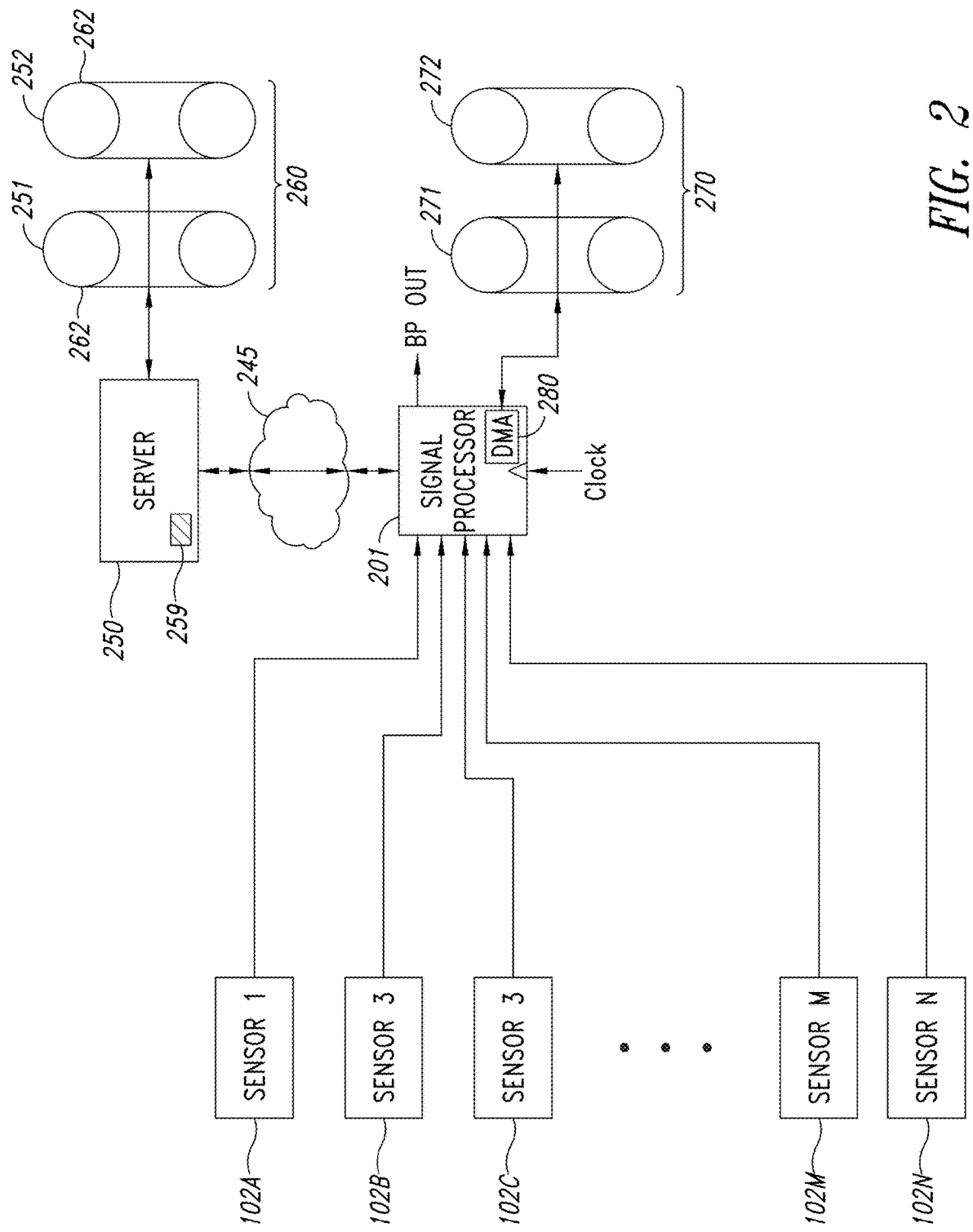
FIG. 2 is a functional block diagram of the cuff-less blood pressure measurement system.

Referring now to FIG. 2, the plurality of bio-sensors 102A-102N are coupled in communication with the signal processor 201 of a BP scanner (or vital signs scanner) 101. A server 250 with one or more remote BP databases 260 is periodically coupled in communication with the signal processor 201 over one or more networks 245, such as the internet, wireless local area network, and/or Bluetooth network. The server 250 includes one or more processors 259 and one or more storage devices 262 to store the one or more BP databases 260, as well as applications and firmware. The applications support the databases, the signal processor 201, and the centralized portable BP scanner 101. The one or more remote BP databases 260 can store biometric information provided by users, physiological information of users captured by centralized portable BP scanners 101 and the plurality of bio-sensors 102A-102N during reference BP scans, and associated reference BP measurements of users. Initially, one of the one or more remote BP databases 260 store a seed BP database of seed BP data The BP scanner 101 may include storage devices that store one or more local user BP databases 270 coupled in communication to the signal processor 201. Alternatively, the storage devices may be in a local computing device, such as a smart phone. The server may also allocate a portion of the capacity of a storage device to securely maintain the data of the one or more local user BP databases. Similar to the one or more remote BP databases 260, the one or more local BP databases 270 can store biometric information provided by the user, physiological information captured by the centralized portable BP scanner 101 and the plurality of bio-sensors 102A-102N during reference BP scans, and reference BP measurements of the user. The signal processor 280 may include a direct memory access (DMA) engine 280 to more quickly transfer blocks of data between the BP scanner 101, the one or more local BP databases 270, and the one or more remote BP databases 260.

The plurality of bio-sensors 102A-102N are energized by the signal processor 201 at the start of a BP scan. The corresponding signals sensed by each bio-sensor are measured simultaneously over the same time during the BP scan. The sensed signals from each bio-sensor are coupled into the signal processor 201 and synchronized in time by the same clock signal CLOCK. As its name suggests, the signal processor 201 processes the sensed signals from the plurality of bio-sensors 102A-102N.

In accordance with an adaptive BP model and its coefficients or parameters, the signal processor 201 generates a gauge, a prediction, or a statistical inference of blood pressure (diastolic and systolic) of the user in response to the sensed signals at the biosensors. The blood pressure values output by the signal processor 201 may be absolute values of blood pressure, relative change in blood pressure, or both absolute and relative change in blood pressure.

Figure 3:
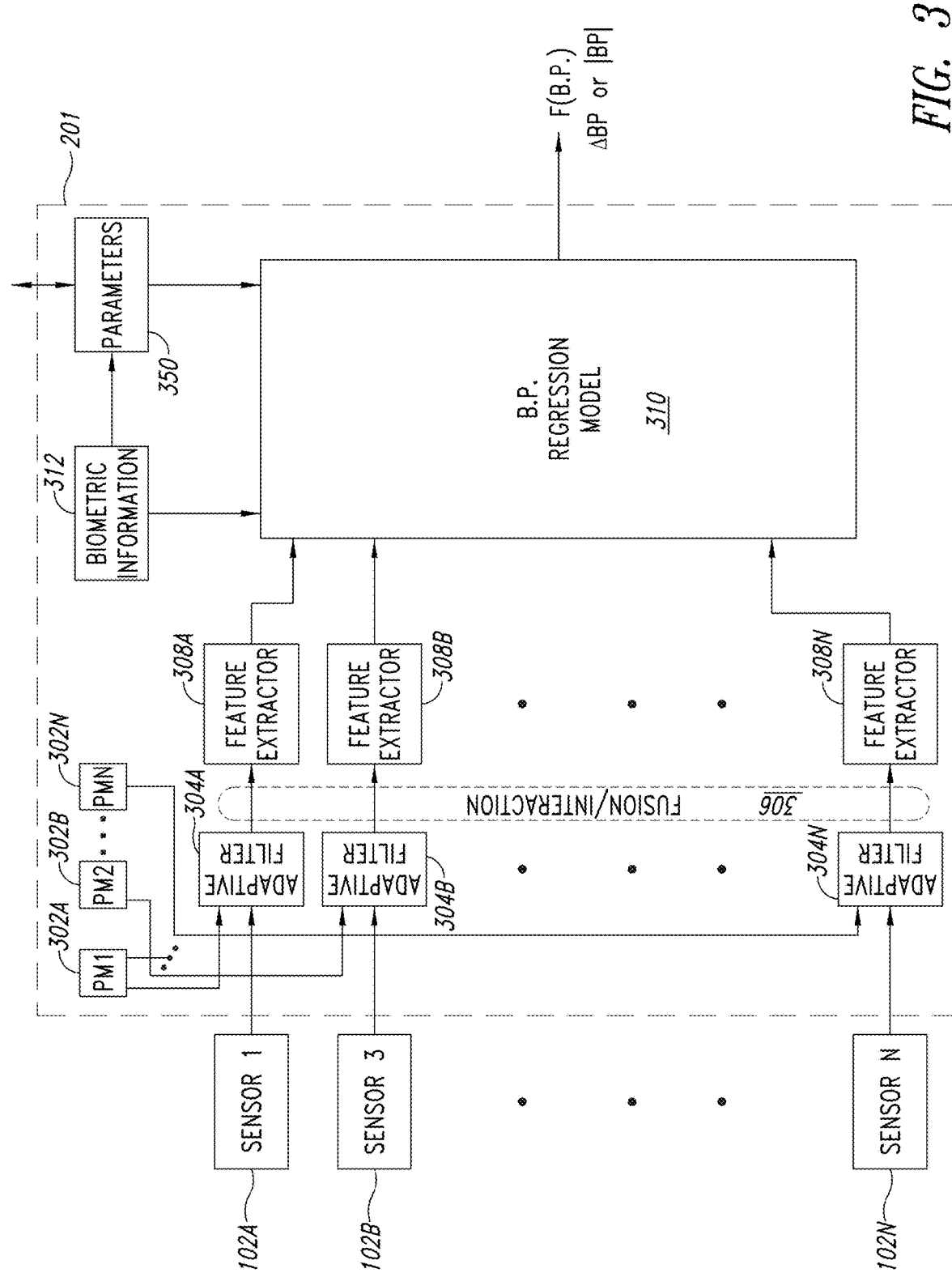
FIG. 3 is a functional block diagram of signal processing performed by the signal processor to non-invasively calculate blood pressure.

Referring now to FIG. 3, a functional block diagram of the signal processor 201 is shown coupled to the plurality of bio-sensors 102A-102N. The sensed signals from the bio-sensors 102A-10N are respectively coupled into a plurality of adaptive filters 304A-304N, such as a Kalman Filter (KF) or an Extended Kalman Filter (EKF). The plurality of adaptive filters 304A-304N are responsive to respective physiology-based models 302A-302N of what feature is being extracted and what is being captured. The sensed signals are processed by the adaptive filters 304A-304N with use of the respective underlying physiology-based models 302A-302N to detect desired signals.

Various physiological features are extracted from the processed signals by feature extractors 308A-308N. The plurality of extractors 304A-304N are programmed by the BP model to extract the desired physiological features for the BP model 310. In this manner, if the BP model is updated to use additional physiological features, then the signal processor 201 is adaptable to the updated BP model. Exemplary physiological features that are extracted include quantities with direct physiological interpretations (e.g., pulse width transit (PWT) time, heart rate (HR), pulse rate (PR), duration of the systolic and diastolic phases, properties of P, Q, R, S, T segments of the ECG waveform, etc.), as well as mathematical features describing the signals (such as: magnitudes and phases of signal components after decomposition into Fourier series, correlation with principal components of the signals, signal histograms, auto- and cross-correlations, etc.). One or more of the processes signals may be fused together by fusing/interacting processes 306 to form other signals from which features are extracted. The collection of extracted features from the sensed signals may be referred to as a feature set.

The feature-set of extracted features is augmented with biometric information 312 provided by the user. Biometric features of the underlying user may be extracted from the biometric information 312 provided by the user over time. For example, a user may input his birth date as part of the biometric information 312. For each BP scan, the user's current age may extracted from the user's birth date in response to the current date of the BP scan from a calendar maintained by the signal processor 201.

At the center of the cuff-less BP system, the signal processor 201 includes an underlying adaptive parametric BP model 310 that links the extracted signal features and extracted biometric features with blood pressure. The parametric BP model 310 receives coefficients/parameters 350 and generates a measure or a gauge of blood pressure f(B.P.) (a change in BP, or an absolute BP) in response to the extracted signal features and extracted biometric features. To obtain more accurate measures of blood pressure, the parametric BP model 310 is tuned over time with updated coefficients/parameters 350 as it is used by the user.

Figure 5A:
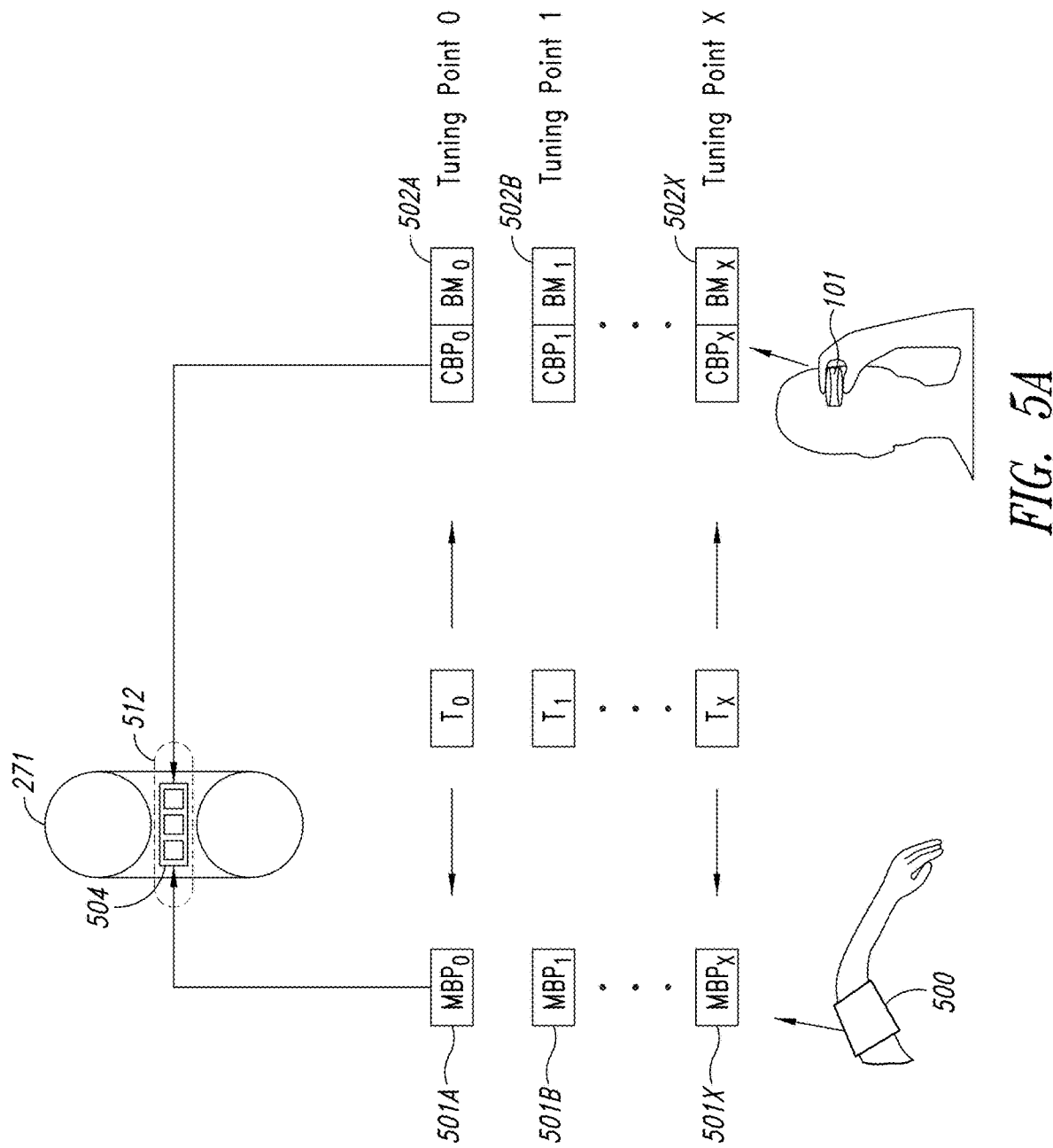
FIG. 5A illustrates tuning of the BP model by capturing one or more reference blood pressure measurements with a blood pressure cuff and pairing them with respective one or more reference blood pressure scans with a cuff-less blood pressure scanner at respective tuning points.

Referring now back to FIG. 2, prior to release of the BP scanner 101 to users, the manufacturer generates a prior seed BP database in the one or more databases 260 associated with an initial BP model in the scanner 101 for determining absolute blood pressure levels. Such as shown in FIG. 5A, a plurality of reference subjects each use a reference BP measuring device, such as a blood pressure cuff 500, to determine measured reference BP (SBP and DBP) levels (reference BP measurements) while at the same time using the BP scanner 101 to perform a reference BP scan to determine an inference or estimate of their blood pressure. The reference subjects may be selected to provide a wide range of biometric information for the measured reference BP and the reference BP scan. A large number of reference subjects performing paired reference BP scans and reference BP measurements in a seed BP database is useful in determining absolute blood pressure values for a wide range of users of the BP scanner.

A plurality of reference BP measurements and reference BP scans may be performed on each subject during different times of the day. Over a period of time, a subset of the reference subjects perform a large number of paired reference BP scans and reference BP measurements. The large number of paired reference data per subject in a seed BP database is useful in determining calculated changes in blood pressure values from scan to scan during different times of the day for users of the BP scanner.

As shown in FIG. 2, for each reference BP scan and reference BP measurement, one of the prior seed BP databases 251 stores the raw signals from the plurality of bio-sensors 102A-102N, the measured reference BP levels, and biometric information of the subject for each entry of paired reference data. Another prior seed BP database 252 stores the physiological signal features extracted from the sensor signals by the extractors, the measured reference BP levels, and biometric information of the subject for each entry. The portion of the data in the seed BP database 252 that is downloaded into a BP scanner may generally be referred to herein as seed BP data or simply see data. While biometric information about the plurality of subjects is available in the databases, the identity of the plurality of subjects is not. Anonymous subject identification (ID) (e.g., a numeric ID or an alpha-numeric ID) is used for each database entry so that the subjects remain anonymous in the one or more seed BP databases to all users.

The data for machine learning of parameters/coefficients to tune a BP model for statistical inference of blood pressure levels of a user are now described in more detail.

Parameter Determination for Blood Pressure Model

Referring now to FIGS. 4, 5A-5B, and 6A-6C, the coefficients (parameters) 350 of the BP regression model 310 are determined via machine learning techniques (such as: Linear Regression, Polynomial Regression, Support Vector Machine, Random Forrest, Neural Networks, etc.). The machine learning is performed progressively over several phases generating an evolving BP model 310 with increasing accuracy.

Figure 4:
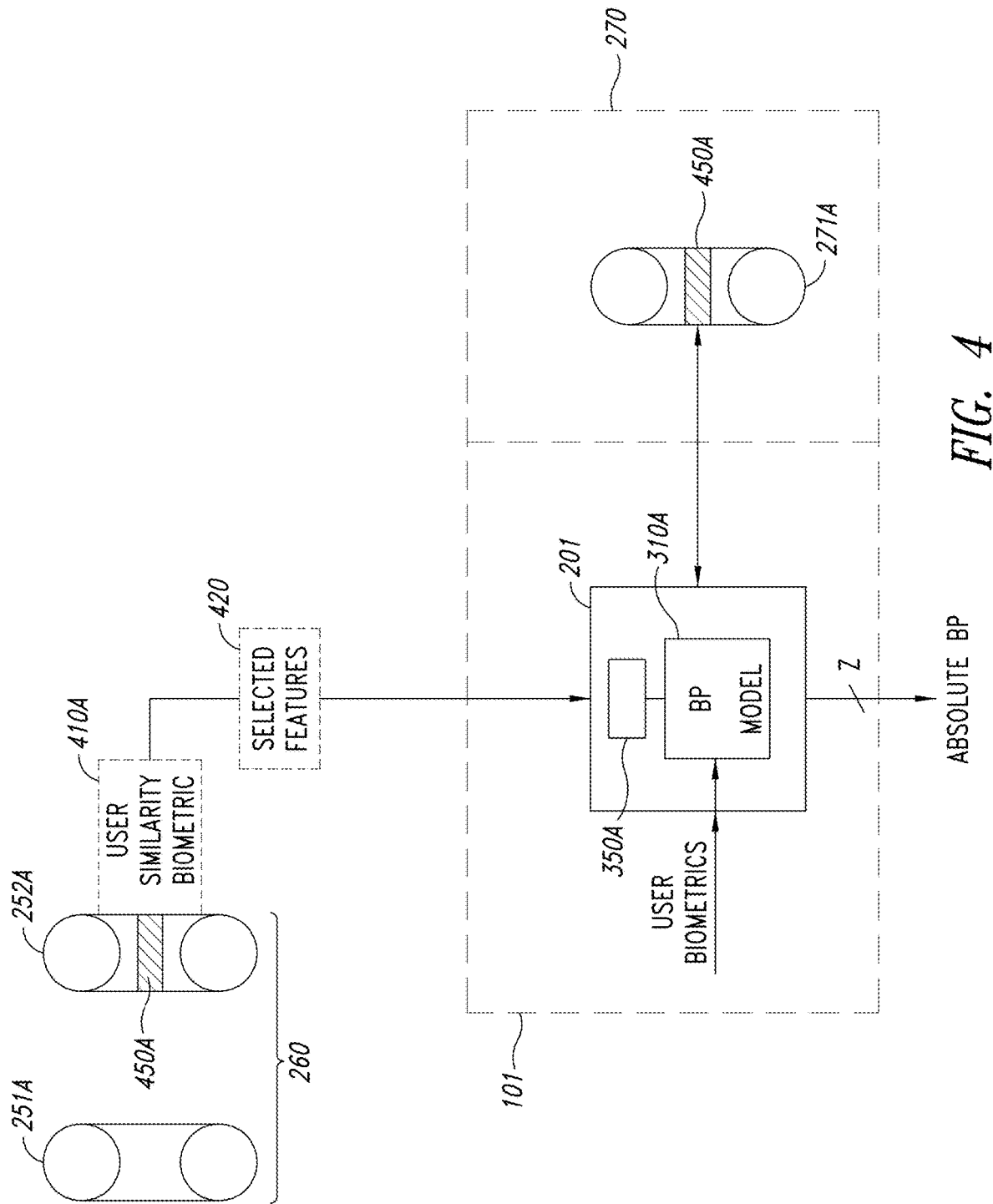
FIG. 4 illustrates a functional block diagram of downloading seed BP data into the scanner from which parameters/coefficients are selected to non-invasively calculate a measure of blood pressure without using any reference measured blood pressure to tune them.

With reference to FIG. 4, coefficients (parameters 350A) for the first initial BP model 310A are derived from a large remote seed BP database 252A of BP scans paired with blood pressure levels measured using a reference device. The seed BP database 252A includes a large number of subjects with diverse levels of blood pressures and diverse biometrics. At this point, there is no calibration or tuning of the parameters of the BP model 310A and its regression algorithm to the user's measured blood pressure levels of diastolic and systolic blood pressure. Accordingly, the initial BP model 310A has the capability to infer the user's blood pressure with limited accuracy.

The seed BP database 252A includes data from a large number of human subjects (a function of model complexity—generally at least ten times the number of parameters or variables, e.g., greater than 100) with diverse levels of blood pressures and diverse biometrics (e.g., age, sex, weight, height, body-mass-index (BMI), smoking, non-smoking, waist circumference, etc.). A subset of the seed BP database 252A, referred to as seed BP data 450A from seed scans, is used to for selecting and updating or tuning the parameters 350A and the BP model to the user. The seed BP data 450A is selected from the seed BP database 252A based on similarities with the user.

Initially, similar biometrics (e.g., age, sex, weight, height, body-mass-index (BMI), smoking, non-smoking, waist circumference, etc.) are used to select the seed BP data 450A. As reference blood pressure measurements are taken of the user, similar systolic and diastolic blood pressures (or user's distribution of the reference blood pressure from the tuning points) may also be used to refine the seed BP data for tuning the parameters of the BP model to the user. As more user information is gathered by the BP scanner 101 during BP scans, similar extracted signal features (e.g., user's distribution of signal features from all scans) may also be used to refine the seed BP data for tuning the parameters of the BP model to the user. Accordingly, a filter 410A with various user information may be used to search the seed BP database 252A for seed BP data to initialize and tune the parameters 350 of the BP model 310.

Furthermore, not all the extracted signal features may be needed to tune the parameters and model. A relevant subset of extracted signal features from the seed BP database may be used to tune the parameters 350 of the BP model 310. Accordingly, a second filter 420 with the relevant signal features that are desired may be used to limit the amount of seed BP data that is download from the seed BP database 252A to tune the parameters 350 of the BP model 310. This can save download time and reduce storage capacity usage in the local storage device used to store the seed BP data 450A. If sufficient storage is available in the local reference BP database 271A, the second filter 420 may not be needed and all the extracted signal features in the similar seed BP data may be downloaded and stored.

Occasionally, the manufacturer of the BP scanner 101 may update the seed BP database with significant changes. The BP scanner 101 may recognize the significant change and download the updates on its own. Alternatively, the manufacturer of the BP scanner 101 can push out the update in the seed BP database to all users and force an update of the seed BP data 450A used by the BP scanner. The BP model in the BP scanner 101 may be updated by software or firmware updates. The update to the BP model may require users to re-download the seed BP data 450A used by their BP scanner.

The initial BP model 310A and coefficients (parameters) 350A derived from the seed BP data 450A can infer the absolute values of a user's blood pressure from each BP scan with the plurality of sensors. While the absolute values of the user's blood pressure may be accurate for a general health scanner, absolute values of the user's blood pressure may not be sufficiently accurate for a medical BP scanner or a medical vital signs scanner without further tuning.

Referring now to FIG. 5A, additional phases of parameterization for the blood pressure model involve periodically tuning the parameters of the BP model with one or more blood pressure measurements (reference measured blood pressure, MBP0 501A through MBPx 501X, generally referred to with MBPx 501X) captured with a blood pressure cuff 502 or other accurate means of BP measurement. The one or more reference blood pressure measurements MBP0 501A through MBPX 501X are paired with respective one or more reference blood pressure scans (reference BP scans of reference scanned signal features, CBP0 502A through CPBx 502X, generally referred to by CPBx 502X) that are taken with the cuff-less blood pressure scanner 101 at respective tuning points T0 through TX.

Each of the reference blood pressure measurements MBPX 501X are levels of SBP and DBP captured with the blood pressure cuff 502 or other accurate means of BP measurement. Each of the reference scanned signal features CPBx 502X includes the calculated or inferred SBP and DBP (or their calculated changes) and extracted signal features from the signals sensed by the bio-sensors. The biometric data BM0 through BMx (generally referred to as BMx) of the user is included with each of the reference BP scans CPBx 502X. The biometric data BMx of the user is expected to either stay constant (e.g. sex, height) or change slowly over time, such as over several months or years. The blood pressure measurements and the scanned or calculated blood pressure values are expected to change over time of day as well as on a daily basis from scan to scan. The blood pressure measurements and the scanned or calculated blood pressure values may also have long-term trends as the user ages. The extracted signal features in each BP scan are also expected to vary from scan to scan. Accordingly, the biometric data BMx of the user will seem to be relatively constant in comparison with the daily variations in the blood pressure values and the extracted signal features.

The paired reference measured blood pressure MBPx and reference scanned signal features CBPx are stored together along with the biometric data BMx at each tuning point (date/time stamp) as paired reference data 504 into a local reference database 271. Each of the paired reference data of the measured blood pressure MBPx and reference scanned signal features CBPx including biometric data associated with the user are stored with the tuning point (date/time stamp) in the local reference database 271 as user labeled BP data 512. That is, the local reference 271 database stores entries of user labeled data 512 with date/time stamp, biometric information, extracted signal features, and measured blood pressure (SBP and DBP).

The user labeled BP data 512 stored in the local reference database 271 may be periodically uploaded to the seed BP database maintained by the server 250. This expands the seed BP database over time with more seed BP data and possibly a wider range of biometrics being associated with the added BP data. The seed BP database similarly stores entries of seed labeled BP data 450 from the anonymous subjects with date/time stamp, biometric information, extracted signal features, and measured blood pressure (SBP and DBP) but further includes a unique anonymous subject identifier (subject ID) tagged to it.

A new user may elect to become an anonymous subject of the seed BP database by anonymously contributing his/her user labeled BP data 512 to the seed BP database going forward. If so, the user is assigned a unique anonymous subject identifier (subject ID). Periodically, when the BP scanner 101 is in communication with the server 250, the user labeled BP data 512 may be tagged with the subject ID and uploaded to the seed BP database as seed BP data. The subject ID facilitates counting the quantity of seed BP data (e.g., the number of paired reference data) contributed by a subject to the seed BP database. The ratio of quantity of seed BP data per subject may be used as one filter factor in downloading seed BP data from the seed BP database.

Figure 5B:
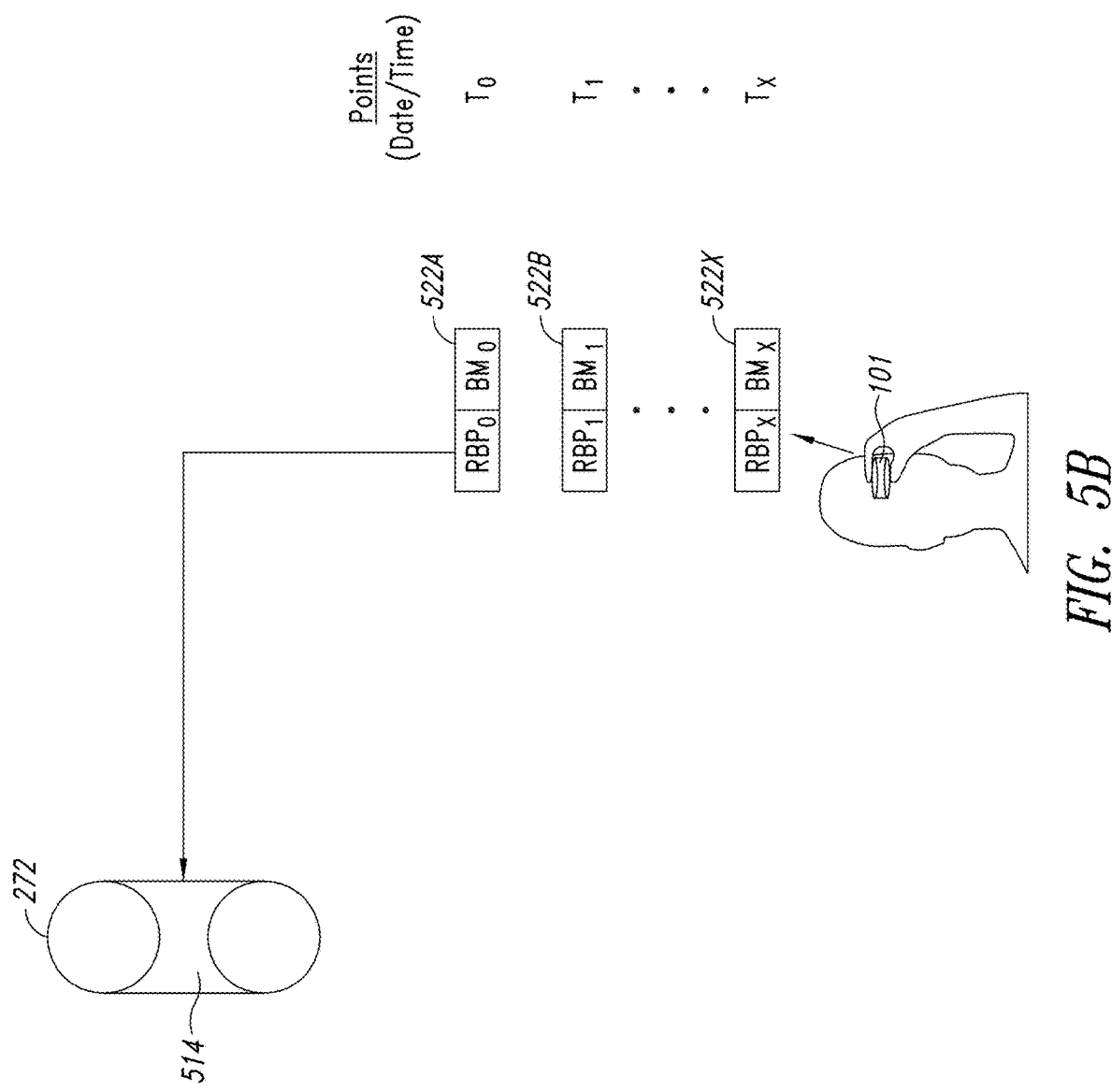
FIG. 5B illustrates taking one or more regular blood pressure scans with a cuff-less blood pressure scanner at respective scanning points (dates and times) without a paired reference blood pressure measurement with a blood pressure cuff.

Referring now to FIG. 5B, other BP scans may be made with the cuff-less blood pressure scanner 101 at a variety of dates/times t1-tx but unassociated with any reference measured blood pressure. These unpaired BP scans may be referred to as regular BP scans 522A-522X and stored in the local regular scan database 272 as user unlabeled BP data 514. Each entry of a plurality of user unlabeled BP data 514 includes a date/time stamp, biometric information, extracted signal features, and inferred blood pressure values (SBP and DBP). Without a paired reference measured blood pressure, the extracted signal features in the regular BP scans 522A-522X are not critical to machine learning and tuning of the BP model. However, the paired reference data of the user labeled BP data 512 stored in the local reference database 271 may be used to tune the BP model.

Figure 6A:
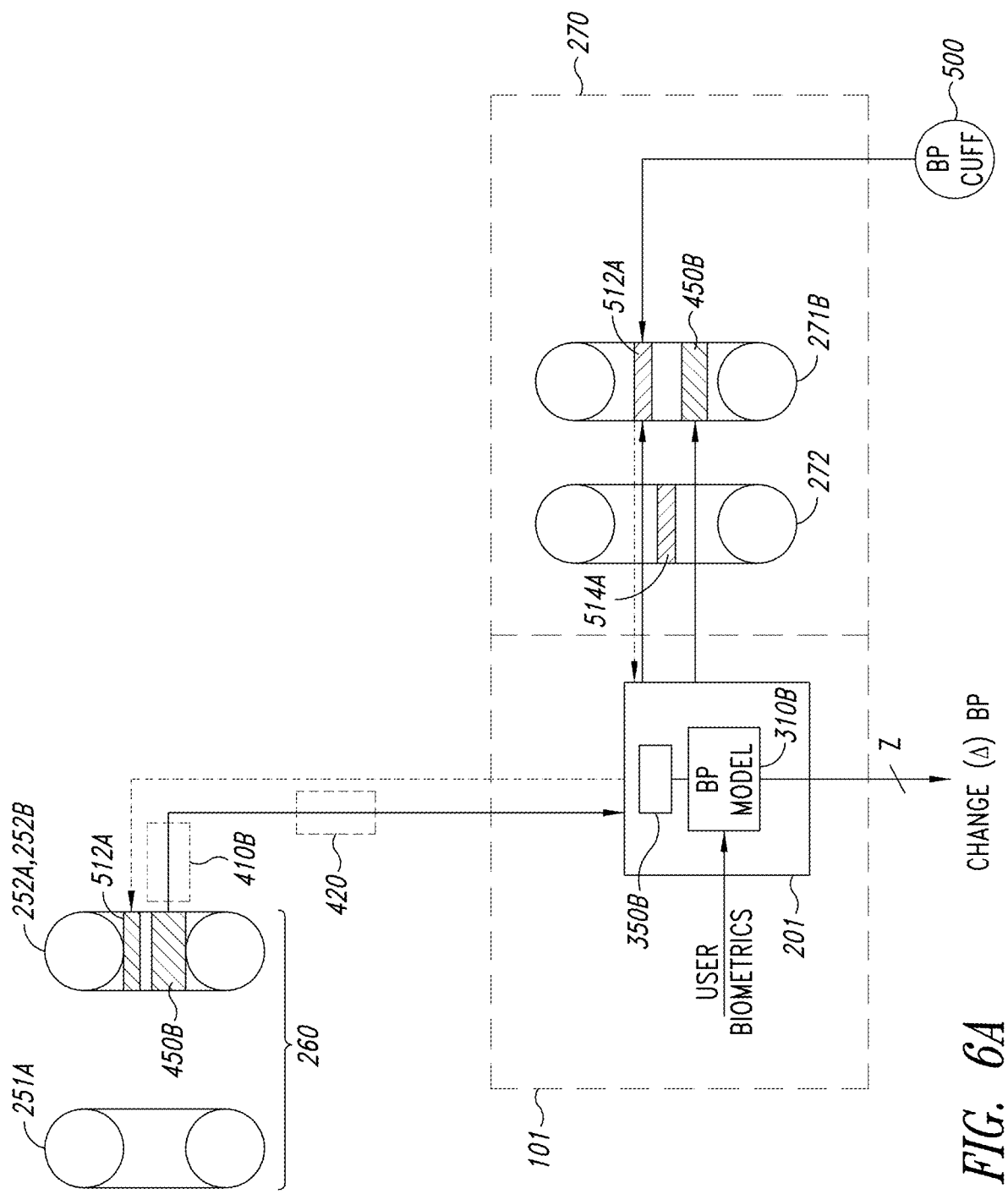
FIGS. 6A-6C illustrate functional block diagrams of the BP scanner and databases, from which parameters/coefficients are selected to tune an adaptive BP model to non-invasively calculate a measure of blood pressure.

Referring now to FIG. 6A, coefficients (parameters 350B) for the second initial BP model 310B are also derived from the large seed BP database 252A. The BP model 310B does not determine absolute blood pressure levels. Instead, the BP model 310B infers the relative blood pressure changes ($\Delta$BP including $\Delta$SBP and $\Delta$DBP) from the last scan. The relative blood pressure changes inferred by the BP model 310B are more reliable and accurate than the absolute blood pressure values inferred by the BP model 310A and its parameters 350A. The second initial BP model 310B utilizes the same seed BP database 252A. However, the downloading of seed BP data 450B from the seed BP data is more selective with a filter 410B. The selected seed BP data 450B that is downloaded with the search filter 410B is from subjects similar to the user, like filter 410A, but with subjects that also have a large number (e.g., greater than 10) of paired reference data stored as seed labeled data in the seed BP database. That is, the seed BP data 450B that is selected for downloading has a scan frequency ratio of scans per subject greater than a predetermined number (e.g., 10). The subject ID is used to determine the ratio in the seed BP database for each subject. This seed BP data 450B with a greater scan frequency ratio better supports tuning of the BP model 310B to calculate and infer a change in blood pressure values from one scan to the next.

To support the BP model 310B, the local reference database 271B may also include a number of user labeled data 512A (paired reference data of extracted signal features with measured blood pressure values). The quantity of user labeled data 512A for a new user is initially limited to just a few because he/she has not yet had a chance to perform many reference scans and reference measurements to generate user labeled data. Over time, it is expected the quantity of user labeled data becomes more in balance with the quantity of seed labeled data downloaded from the seed BP database.

With the limited number of user labeled scan data 512A and the downloaded seed BP data 450B stored in the local reference database 271B, the BP model 310B and its parameters 350B can be tuned in response thereto to better estimate changes in user's blood pressure from one scan to the next. Combing the calculated change in BP from the BP scan with a recent blood pressure measurement with a blood pressure cuff, a reasonable prediction of blood pressure may be made from a BP scan with the BP scanner without using the blood pressure cuff.

Figure 6B:
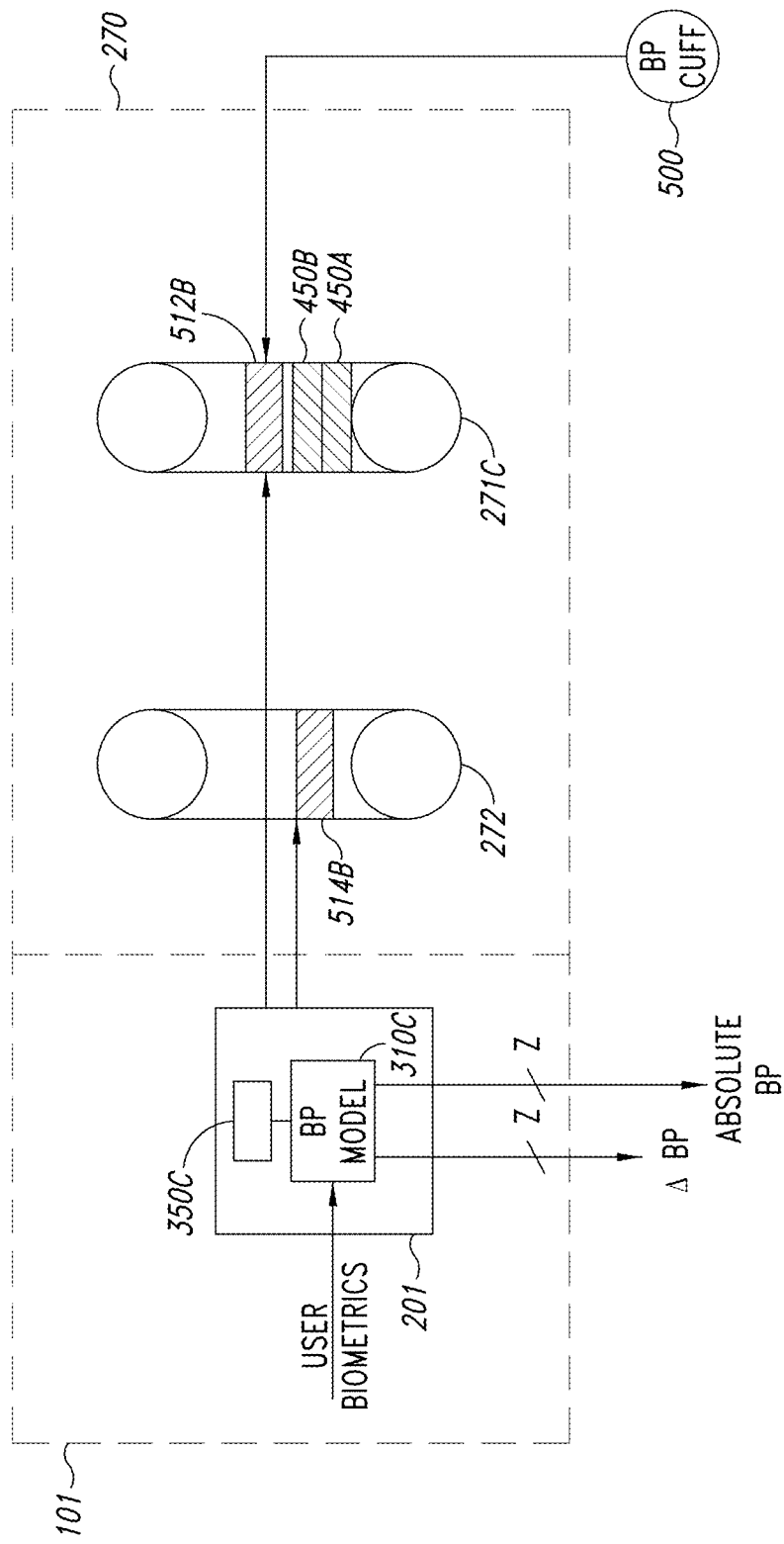

Referring now to FIGS. 6B and 5A, a new BP model 310C with initial coefficients (parameters) 350C may be downloaded from the server into the BP scanner 201. The new BP model 310C combines the prior models 310A,310B together as one to improve upon accuracy in calculations of the inferences in absolute blood pressure levels (SBP, DBP) and changes ΔBP in blood pressure levels (ΔSBP and ΔDBP).

At each tuning point T0 through TX in FIG. 5A, when the user performs a BP scan with a scan device 101 and measures blood pressure with a reference BP measuring device, such as a the blood pressure cuff 500, new user-specific information becomes available. A single tuning point (e.g., T0), if used alone, is insufficient to adjust either BP model for inference of absolute blood pressure with much better accuracy. However, when paired (assuming an adequate balance) with prior BP models 310A,310B and downloaded seed BP data, such as the seed BP data 450A and seed BP data 450B from the seed BP database 252A; and the expanded user labeled data 512B stored in the local reference database 271C; the new BP model 310C with its tuned coefficients (parameters) 350C becomes more accurate.

Moreover, the additional measured reference blood pressure MBPx and associated biometric information BMx captured by the user as user labeled data 512B may be used to adequately re-weight samples in the seed BP data 450A in the formation of parameters (coefficients) 350 for the BP model 310C according to their similarity to the expanded user labeled data 512B. In this manner, the prior absolute BP model 310A may also be adjusted with new parameters, better tuned to the user measured referenced blood pressure MBPx, which further increases accuracy of BP inference of the overall BP model 310C.

Figure 6C:
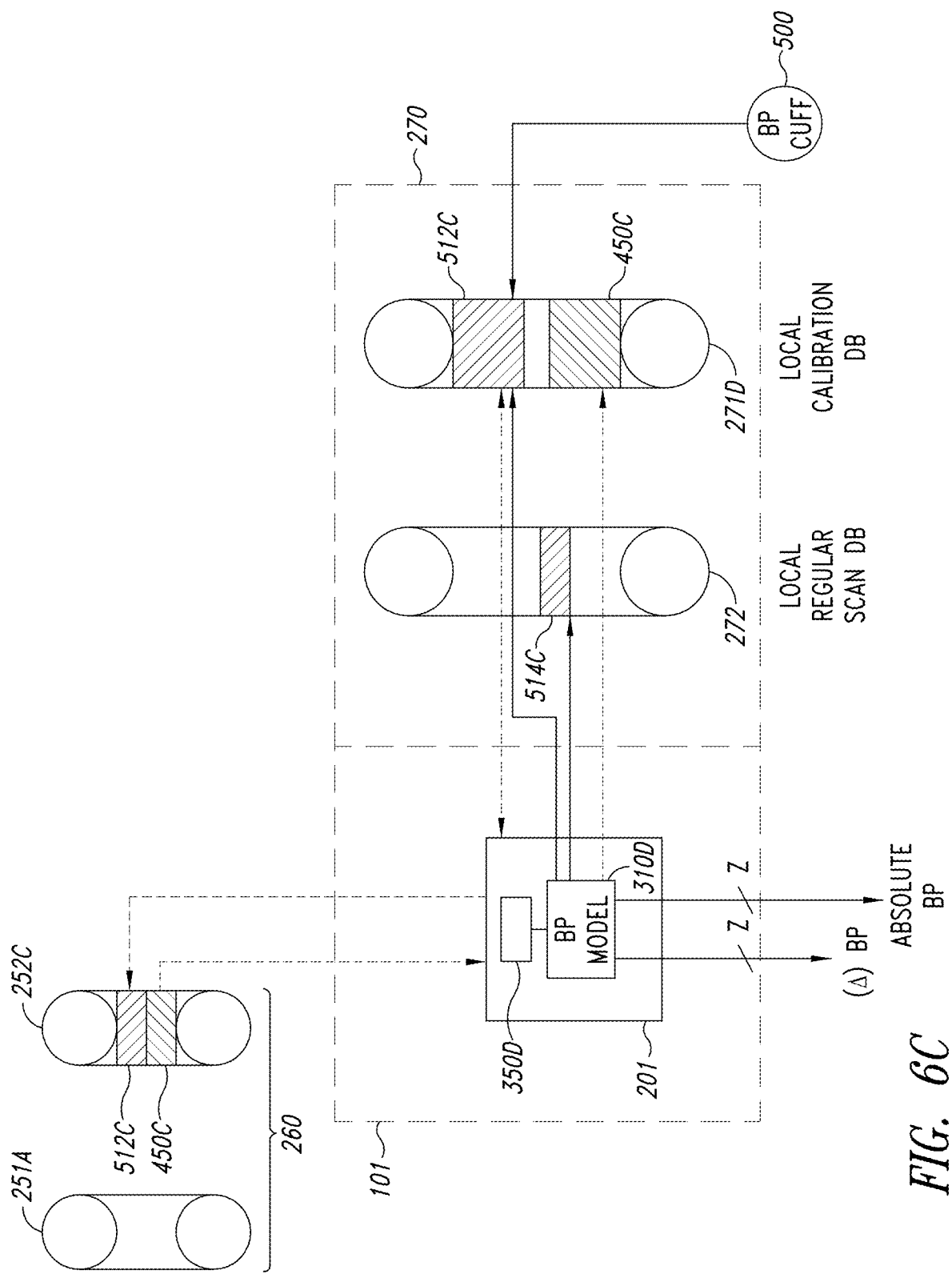

Referring now to FIGS. 6C and 5A, the seed BP databases and the local databases are not static but evolving. The local reference database evolves as more user paired reference data is captured from the reference blood pressure measurements MBPx and scanned features CBPx; associated together with the user as labeled user data 512C and stored in the local reference database 271D. As more users elect to become anonymous subjects of the seed BP database, the seed BP database evolves as their user labeled data 512C is periodically uploaded to the seed BP database 252C as an anonymous contribution, such as when the BP scanner 101 is in communication with the server 250.

With every additional tuning point of the BP scanner 101 to the user, more user-specific information becomes available. The additional user labeled data is added (with adequate weights) to the initial dataset of user labeled data (e.g., 512A,512B) to become a larger set of user labeled data 512C. The larger set of user labeled data 512C can be used to improve the BP model and its calculation of absolute blood pressure levels. The BP model 310D is further tuned by coefficients (parameters 350D) as time goes on with the additional data (e.g., from additional tuning with additional reference BP scans and additional reference BP measurements) in the set of user labeled data 512C, providing further accuracy improvements.

It is desirable to balance the amount of expanded user labeled data 512C with an expanded amount of seed BP data from the seed BP database 252C. Additional seed BP data may be downloaded from the seed BP database 252C to the local reference database 271D as seed BP data 450B. As time goes on the user may age such that the users biometric information may change. The filters 4410A,410B used to search the seed BP data base can adapt to the change in biometric information to pull more relevant seed BP data from the seed BP data base. The additional seed BP data may be filtered to the updated biometric information of the user.

In order to provide a relatively good accuracy level at the early stage of usage by a new user, the BP scanner and its BP model may be tuned several times during the first day (or the first few days). After this initial period, additional tunings may be performed by the new user at a rate from once per three days to once per week. Determinations may be automatically made if the BP scanner and its BP model is out of tune and in need of new tuning points. After performing a sufficient number of tunings, the system learns enough about the new user such that further tuning points may not be necessary.

Tuning Process

Figure 9:
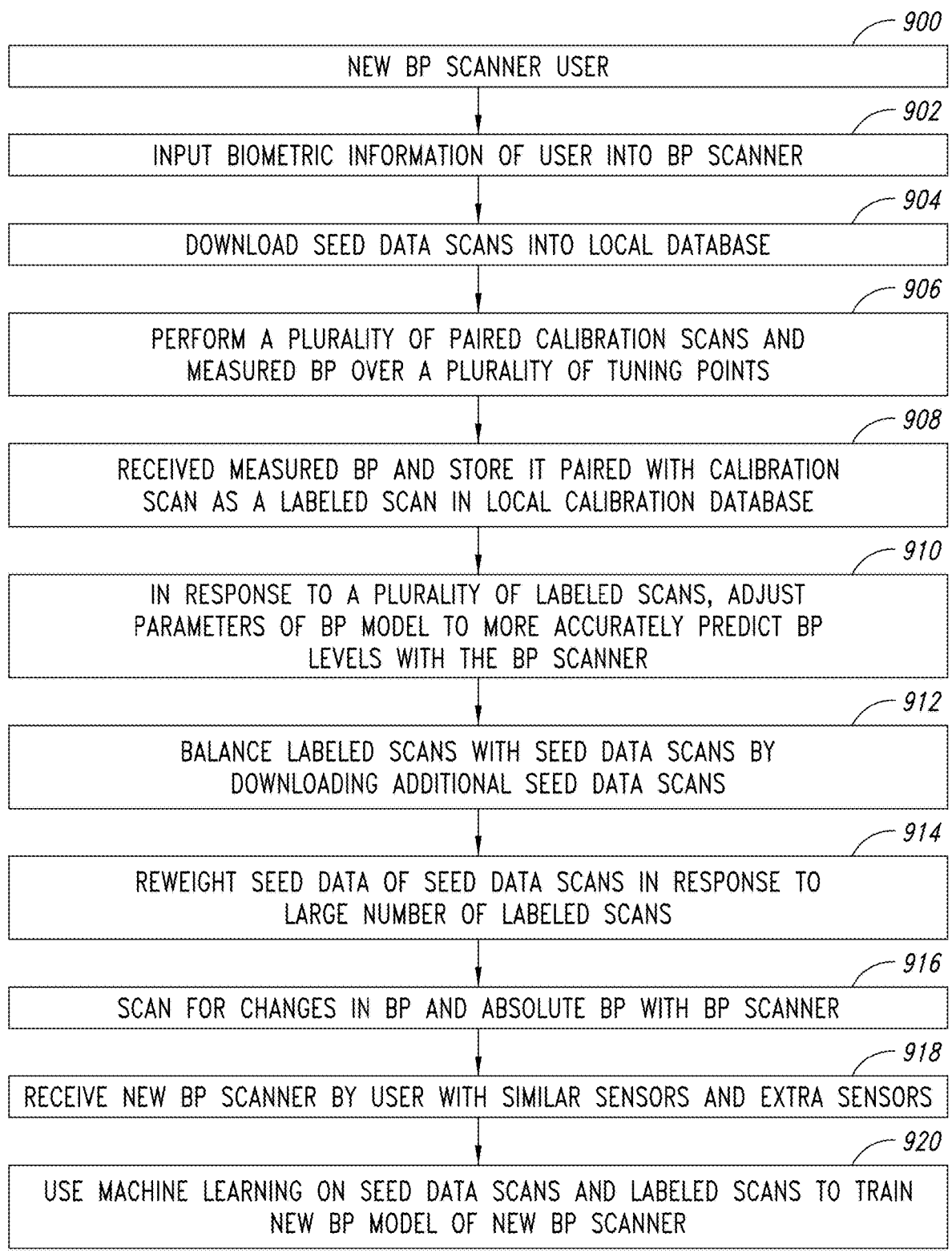
FIG. 9 illustrates a flow chart of tuning the BP model and the BP scanner to a new user with reference scans and reference BP measurements.

FIG. 9 illustrates a flow chart of a new user tuning process 900 of a BP application executed by the signal processor 201, processor 259 of the server 250, or other processor of a computing device. The tuning process 900 customizes the parameters of the BP model to each user and may be referred to as a parameter tuning process. The tuning process 900 of the BP application begins with the login of a new BP scanner user and goes to process 902.

At process 902, biometric information of the new user is entered and read by the BP scanner.

At process 904, seed BP data from seed scans of anonymous users is downloaded from the remote BP databases into the local database of the BP scanner.

At process 906, a plurality of paired reference scans and measured reference BP measurements are made over a plurality of tuning points. The levels of SBP and DBP of the measured reference BP measurements may be manually input into the local database through a user interface. Alternatively, with a BP cuff in communication with the BP scanner, the levels of SBP and DBP of the measured reference BP measurements may be automatically coupled to the BP scanner and loaded into the local database.

At process 908, the measured reference BP is received by the BP scanner and stored in a paired format with the reference BP scan. The paired data is stored as a labeled scan in the local reference database.

At process 910, in response to the plurality of labeled or reference scans, the parameters of the BP model may be updated to more accurately predict BP levels with the BP scanner.

At process 912, the number of labeled (user BP) scans of the user are balanced with the number of seed data scans from the seed subjects. Additional seed BP data associated with seed data scans may be downloaded to balance out the numbers.

At process 914, seed BP data of the seed data scans are reweighted in response to a large number of labeled scans.

At process 916, BP scans are preformed by the BP scanner to predict or infer values for change in blood pressure and values of the absolute blood pressure for a user.

At process 918, a new BP scanner is received by the same user. The new BP scanner has similar sensors to the prior BP scanner. The new BP scanner can also have additional sensors over that of the prior BP scanner. The prior scan data captured with the prior BP scanner of a user can be used to train the new BP scanner to the same user.

At process 920, machine learning is used on the saved seed data scans and the labeled user scans to train the new BP model of the new BP scanner.

BP Calculation Process

Figure 8:
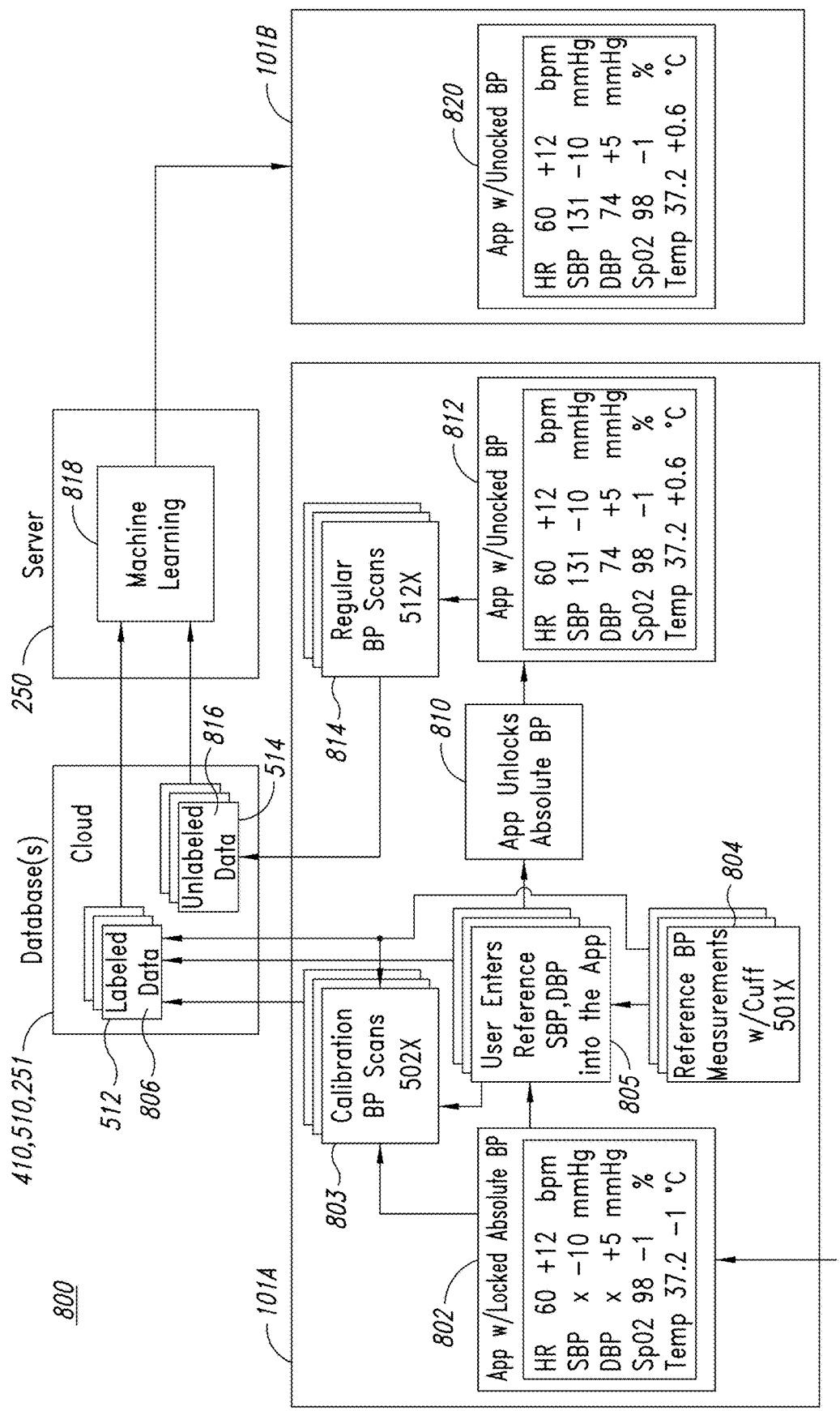
FIG. 8 illustrates a flow chart of the BP model and the BP scanner being used to calculate absolute levels of BP.

FIG. 8 illustrates a flow chart of a BP calculation process 800 of a BP application (app) executed by the signal processor 201. The BP calculation process 800 adapts as the parameters of the BP model are tuned to the user. The process 800 may interface with the server 250 and its associated one or more BP databases. The server 250 and its one or more processors 259 may execute a machine learning process 818 of a software application to tune the BP model of a new BP scanner to the same user with less effort.

At process 801, an initial BP measurement may be made with a blood pressure cuff or other more accurate means of determining systolic blood pressure (SDB) and diastolic blood pressure (DBP).

At process 802, the initial BP measurement may be input into the BP application and locked as the initial absolute BP for the BP scanner 101. If the initial BP measurement is not loaded, the SBP and DBP values are not shown by the scanner until sufficient reference BP scans 502X and reference BP measurements 501X are paired together and stored in the database to allow the BP model to determine a measure of absolute SBP and DPB levels.

At processes 803 and 804, one or more reference BP scans 502X may be made while concurrently taking one or more respective reference BP measurements 501X with a blood pressure cuff at one or more tuning points.

At process 805, the one or more respective reference BP measurements 501X may be manually or automatically entered into the BP application.

At process 806, the one or more reference BP scans 502X are paired with the one or more respective reference BP measurements 501X with the blood pressure cuff and stored into the BP database 251,510 as labeled user BP data 512.

While the absolute BP is locked by the BP application, the BP scanner 101 may determine changes in the absolute BP and show those changes to the user.

At process 810, after a number of pairings of a plurality of reference BP scans 502X and a plurality of respective reference BP measurements 501X taken at different times and possibly different dates, the BP application unlocks the absolute BP stored by the BP application and scanner. This provides a state of the BP application with an unlocked BP 812. In this state, the BP model is well tuned so that it may perform regular BP scans and calculate absolute BP.

At process 814, in the unlocked BP state 812, the BP application can perform one or more regular BP scans 512X to determine absolute DBP levels and absolute SBP levels that are worth saving into the global seed BP database. The regular BP scans 512X may be monitored for quality and detection of an out of tune condition as further described herein.

At process 816, with the BP model fairly well calibrated, the regular BP scans 512X stored in the local regular database of the BP scanner 101A may be periodically uploaded into a global database as unlabeled data 514 to make the global seed BP database larger.

At process 818, a machine learning process may be performed over the unlabeled data 514 in response to the labeled user data 512 to calibrate/tune the parameters/coefficients of a new BP model for a new BP scanner 101B.

The BP scanner device 101B may have a second set of a plurality of sensors greater in number than the number of sensors used by the scan device 101A to generate additional physiologic features to calculate blood pressure. The additional sensors can provide additional signals that may be fused together to improve accuracy of the BP model. Regardless, the prior sensor data and the prior reference scans in the database associated with the prior BP scanner 101A can be used to generate the parameters/coefficients for the new BP scanner 101B to more accurately calculate absolute BP, in a state of the BP application with an unlocked BP 820. This avoids the same user from having to retrain the new scanner 101B with a lot of new reference scans.

Automated Out of Tuning Detection

Figure 7:
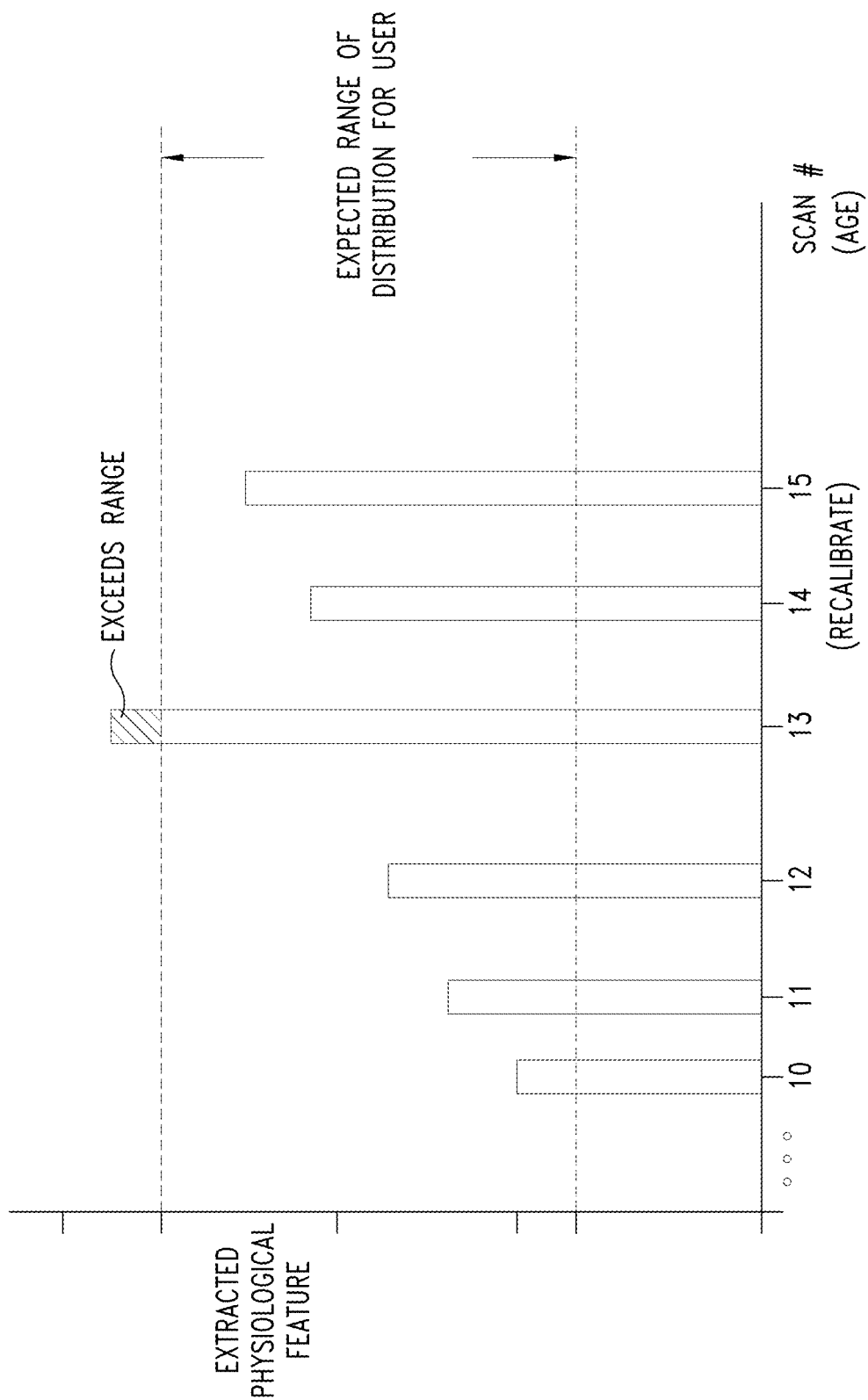
FIG. 7 illustrates an exemplar histogram of an extracted physiologic feature that may be made over each blood pressure scan to detect when the blood pressure model is out of tune.

Referring now to FIG. 7, histograms for each extracted physiologic feature may be made over each blood pressure scan to detect when the blood pressure model is out of tune. In order to properly support automatic detection of need for a new tuning, historical information on feature distributions (histograms) during past tuning points as well as the histograms for all other scans can be formed. For each new scan, the relevant extracted features can be compared with the histograms. An expected range of distribution of each extracted physiologic feature may be formed for the user.

If a new scan extracts features that are outside of the expected range (rise above a maximum or fall below a minimum), the extracted feature may be suspect as well as the overall scan. If the extracted feature falls outside of the distribution (referred to as an extrapolation state), a new tuning point may be sought and suggested to the user in order to adjust the BP model back into a tuned stated.

If the extracted feature is within the distribution of the histogram, corresponding to past tuning points, the new scan can be considered sufficiently similar to the training data. This provides a high degree of confidence in the inference of the new blood pressure levels being made by the scan. If the extracted feature falls within the distribution, the system is referred to being in an interpolation state.

Advantages

There are a number of advantages to the blood pressure model and the tuning of its coefficients/parameters by machine learning. The accuracy of the inference of the blood pressure values from the model can improve with subsequent tunings. The blood pressure model is flexible and can be customized to the user to provide better accuracy. With a history of extract features, the relevant features can be monitored to determine if the blood pressure model is out of tune and is desirable to re-tune with a new tuning. After a sufficient number of tunings, the system learns enough about the user, so that accurate inferences of blood pressure may be given without further tuning

CONCLUSION

Various specific materials, designs, dimensions, etc. are provided and are considered highly beneficial embodiments of the present disclosure in one regard. However, in other regard, such specifics are also merely illustrative of broader aspects of the present disclosure and should not be considered to necessarily limit to such broader aspects unless expressly specified to be required. In particular, the various specific dimensions provided as such examples are intended to be about any particular values provided, with typical tolerances and ranges of suitable alternatives as would be apparent to one of ordinary skill. Where particular combinations of such dimensions are provided for exemplary illustration of certain embodiments, the relative relationships between them are also contemplated as having been herein disclosed as additional beneficial aspects (even if the specific values of the relative dimensions change). For example, certain lengths, widths, and/or depths of particular components shown and described for a particular assembly provide overall geometries which may be varied by changing certain sub-sets of such dimensions, but may also be fixed relative to the ratios of these values despite the valued changing (so long as their general relationship remains). Similarly, such dimensions of different component parts also have similar relative relationships which are similarly contemplated, also as apparent to one of ordinary skill.

When implemented in software, the elements of the embodiments of the invention are essentially the code segments or instructions to perform the functional tasks described herein. The code segments or instructions are executable by a processor, such as signal processor 201, or one or more processors 259, and can be stored in a storage device or a processor readable storage medium awaiting execution. The processor readable storage medium may include any medium that can store information. Examples of the processor readable storage medium include an electronic circuit, a semiconductor memory device, a read only memory (ROM), a flash memory, an erasable programmable read only memory (EPROM), a floppy diskette, a CD-ROM, an optical disk, a hard disk. The code segments or instructions may be downloaded via computer networks such as the Internet, Intranet, etc. into the processor readable storage medium.

While certain embodiments of the disclosure have been described, these embodiments have been presented by way of example only, and are not intended to limit the scope of the disclosure. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination. Various combinations and sub-combinations, and modifications as may be made, of the presently disclosed components and embodiments and aspects are contemplated whether or not specifically disclosed hereunder, to the extent and as would be apparent to one of ordinary skill based upon review of this disclosure and in order to suit a particular intended purpose or application.

Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by patented claims that follow below.

What is claimed is:

1. A method for a cuff-less blood pressure scanner, the method comprising:
   receiving biometric information of a user into the cuff-less blood pressure scanner;
   downloading seed blood pressure data from a seed blood pressure database into memory based on the biometric information of the user;
   initializing a blood pressure model of a signal processor in communication with the memory, the blood pressure model being initialized with a plurality of parameters based on the seed blood pressure data; and
   periodically tuning the plurality of parameters of the blood pressure model based on paired reference blood pressure measurements and reference blood pressure scans of the user.

2. The method of claim 1, further comprising:
   initiating a blood pressure scan to generate an inference of absolute blood pressure values of the user with a plurality of bio-sensors.

3. The method of claim 1, further comprising:
   adapting the blood pressure model to a first updated blood pressure model.

4. The method of claim 3, further comprising:
   initiating a blood pressure scan to generate an inference of change in blood pressure values of the user.

5. The method of claim 4, further comprising:
   adapting the blood pressure model to a second updated blood pressure model.

6. The method of claim 5, further comprising:
   initiating a blood pressure scan to generate an inference of change in blood pressure values of the user and an inference of absolute blood pressure values of the user.

7. A method for a cuff-less blood pressure scanner, the method comprising:
   capturing a plurality of synchronized sensor signals with a plurality of biosensors of a cuff-less blood pressure scanner;
   extracting a plurality of physiological features from the plurality of synchronized sensor signals;
   monitoring values of one or more physiological features of the extracted plurality of physiological features over time to determine an expected range of values for the one or more physiological features;
   detecting a value for at least one of the one or more physiological features that is outside the expected range of values for the at least one physiological feature; and
   informing a user to tune parameters of an adaptive blood pressure model associated with the cuff-less blood pressure scanner in response to the value for the at least one physiological feature being outside the expected range of values.

8. The method of claim 7, further comprising:
   performing a reference blood pressure measurement with a blood pressure cuff;

concurrently performing a reference blood pressure scan with the blood pressure scanner; and storing the reference blood pressure measurement and the reference blood pressure scan into a local reference database as a pair of reference blood pressure readings.

9. The method of claim 8, further comprising:

tuning parameters of the blood pressure model based on a plurality of stored pairs of reference blood pressure readings.

10. A cuff-less blood pressure (BP) scanner for gauging blood pressure, comprising:

a plurality of electronic bio-sensors configured to concurrently contact a user and generate a plurality of sensor signals; and a signal processor operatively coupled to the plurality of electronic bio-sensors, the signal processor being configured to (a) simultaneously receive the plurality of sensor signals from the plurality of electronic biosensors synchronized together by a clock signal, (b) extract a plurality of physiological features from the received plurality of synchronized sensor signals, (c) monitor values of one or more physiological features of the extracted plurality of physiological features over time to determine an expected range of values for the one or more physiological features, (d) detect a value for at least one of the one or more physiological features that is outside the expected range of values for the at least one physiological feature, and (e) inform a user to tune parameters of an adaptive blood pressure (BP) model associated with the cuff-less blood pressure scanner in response to the value for the at least one physiological feature being outside the expected range of values, wherein the adaptive BP model is configured to calculate blood pressure of a user based on the extracted plurality of physiologic.

11. The cuff-less BT scanner of claim 10, further comprising, memory coupled to the signal processor, the memory storing anonymous seed BP data and prior user BP data, wherein the calculation of the blood pressure of the user by the adaptive BP model is further based on the stored anonymous seed BP data and prior user BP data.

12. The cuff-less BP scanner of claim 11, wherein the prior user BP data includes a plurality of paired reference data each including measured blood pressure, scanned blood pressure, and biometric data associated with the user.

13. The cuff-less BP scanner of claim 12, wherein the anonymous seed BP data includes a plurality of paired reference data each including measured blood pressure, scanned blood pressure, and biometric data associated with a plurality of anonymous subjects.

14. The apparatus of claim 13, wherein the anonymous seed BP data is selected so that the biometric data associated with the plurality of anonymous subjects is similar to the biometric data associated with the user.

15. The cuff-less BP scanner of claim 10, further including a plurality of adaptive filters operatively coupled to the plurality of electronic bio-sensors, the plurality of adaptive filters being configured to detect a plurality of desired signals in the plurality of sensor signals generated by the plurality of electronic bio-sensors.

16. The cuff-less BP scanner of claim 10, wherein one or more of the plurality of electronic bio-sensors include one of an optical sensor, an electrical sensor, a motion sensor, an acceleration sensor, a piezo-electric sensor, or an acoustic sensor.

17. The cuff-less BP scanner of claim 10, wherein one or more of the plurality of electronic bio-sensors are positioned within a housing of the cuff-less BP scanner and configured to be in wired communication with the signal processor.

18. The cuff-less BP scanner of claim 10, wherein one or more of the plurality of electronic bio-sensors are remotely positioned from the signal processor and configured to wirelessly communicate with the signal processor.

19. The cuff-less BP scanner of claim 10, wherein the signal processor is configured to wirelessly communicate with a smart-phone.

20. The cuff-less BP scanner of claim 10, wherein the cuff-less BP scanner is a portable device.

* * * * *